United States Patent
Cirelli et al.

[11] Patent Number: 5,848,990
[45] Date of Patent: Dec. 15, 1998

[54] DEVICE FOR INTRODUCING ACTIVE SUBSTANCE INTO A PATIENT

[75] Inventors: Giorgio Cirelli, Möhlin, Switzerland; Benno Rothenhäusler, Lörrach, Germany; Hans Steffen, Liestal, Switzerland

[73] Assignee: Hoffmann-La Roche Inc., Nutley, N.J.

[21] Appl. No.: 911,198

[22] Filed: Aug. 14, 1997

Related U.S. Application Data

[63] Continuation of Ser. No. 701,268, Aug. 22, 1996, abandoned, which is a continuation of Ser. No. 574,092, Dec. 11, 1995, abandoned, which is a continuation of Ser. No. 327,534, Oct. 21, 1994, abandoned.

[51] Int. Cl.⁶ .................................................. A61M 37/00
[52] U.S. Cl. ........................................... 604/136; 604/131
[58] Field of Search ..................... 604/131, 132, 604/134, 136, 137, 157; 128/DIG. 12

[56] References Cited

U.S. PATENT DOCUMENTS

| | | |
|---|---|---|
| 4,170,993 | 10/1979 | Alvarez . |
| 4,632,671 | 12/1986 | Dalton . |
| 4,781,688 | 11/1988 | Thoma et al. . |
| 4,886,499 | 12/1989 | Cirelli et al. ............................. 604/131 |
| 4,894,054 | 1/1990 | Miskinyar ................................ 604/136 |

FOREIGN PATENT DOCUMENTS

| | | |
|---|---|---|
| 272530 | 12/1986 | European Pat. Off. . |
| 0239244 | 2/1987 | European Pat. Off. . |
| 0369972 | 11/1989 | European Pat. Off. . |
| 4200595 | 1/1992 | Germany . |
| 222839 | 3/1991 | New Zealand . |
| 81338 | of 0000 | Taiwan . |

OTHER PUBLICATIONS

Abstract (corresponding to DEA 4200595).

Primary Examiner—Ronald Stright
Assistant Examiner—N. Kent Gring
Attorney, Agent, or Firm—George W. Johnston; William H. Epstein; John P. Parise

[57] ABSTRACT

A device for introducing an active substance solution into a patient and with means for fastening to the skin and a cannula. The cannula is held in a withdrawn position by a retaining and releasing mechanism before use and, after release, is propelled into the patient's skin. A connector connected to the rear of the cannula serves to connect the cannula to an active substance reservoir.

10 Claims, 3 Drawing Sheets

DEVICE FOR INTRODUCING ACTIVE SUBSTANCE INTO A PATIENT

This is a continuation of application Ser. No. 08/701,268, filed Aug. 22, 1996, which is a Rule 60 Continuation of Ser. No. 08/574,092, filed Dec. 11, 1995, which is a Rule 62 Continuation of Ser. No. 08/327,534, filed Oct. 21, 1994, all now abandoned.

BACKGROUND OF THE INVENTION

1. Field

The invention relates to a drug delivery device for introducing a pharmaceutically active substance solution into a patient.

2. Description

During the preparation of a patient for an operation and the like, it is customary to create a venous access to which cannula injection appliances can be connected in case of need. However, in the area of after-care, therapy and prevention, this custom is frequently associated with disadvantages. For example, the insertion of cannulas may be performed only by trained medical staff. Patients themselves are in most cases not capable of this, so that self-medication is not possible in the case of medicines which are injected. On the other hand, the insertion of a cannula results, especially in the case of long-term therapy, in an injury with an increased danger of infection. The danger of injury when handling used cannulas represents an additional risk. For cost and safety reasons, these disadvantages lead to the subcutaneous or intradermal injection route frequently being chosen.

Devices which can be worn on the body and which represent a combination of cannula and reservoir for storing the active substance solution have been developed for the patient's convenience, specifically to facilitate self-medication. For example, EP-A-272 530, corresponding to U.S. Pat. No. 4,886,499, (which is incorporated herein by reference) discloses a wearable device for subcutaneous or intradermal injection of a liquid active substance formulation, which consists of a storage reservoir, an injection needle to be connected to the latter, a pump unit for emptying the container through the injection needle and skin fastening means. In the device disclosed in EPA 272530, the needle is propelled by means of a drive device into the skin of the patient.

Devices of this type which have the active substance reservoir as an integral component have the disadvantage that the application of a separate device is necessary for each active substance formulation. In addition, the limitation of the volume of active substance in the reservoir of these devices prevents their use for a number of applications.

SUMMARY OF THE INVENTION

The invention provides a drug delivery device which offers great convenience to the patient and, at the same time, the maximum possible flexibility and safety for intradermal and subcutaneous injections.

This is achieved, according to the invention, by a device for introducing an active substance solution into a patient with means for fastening the device to the body surface and with a cannula for insertion into the skin and for introducing the active substance solution, said device comprising an advancer unit to propel the cannula into the skin, a connecting element which is arranged on the outside of the device for connection to a conveying unit for the active substance solution, a connection channel, which is open in the inserted state of the cannula, between the connecting element and the cannula.

According to a further embodiment of the invention, the said advancer unit is designed in such a way that the cannula can, after the infusion is complete, be returned to a protected initial position.

BRIEF DESCRIPTION OF THE FIGURES

Exemplary embodiments of the invention are described hereinafter by means of the appended drawings wherein:

FIG. 3b shows a groove of FIG. 3a

FIG. 5b shows a cross sectional view of the embodiment of FIG. 5a taken perpendicular to cross section of FIG. 5a.

DETAILED DESCRIPTION OF THE INVENTION

The invention relates to a device for introducing an active substance solution into a patient from a conveying unit, the device including fastening means for fastening to the patient's skin. The device comprises a housing having a central cavity and a base. The device also includes a cannula holder located within the cavity and configured to move from a first terminal position to a second terminal position. The cannula is secured to the cannula holder above the base and dimensioned such that the cannula does not pass through the base when the cannula holder is positioned at its first terminal position and passes through the base and into the patient's skin when the cannula holder is positioned at its second terminal position. The device also includes an advancer means within the cavity for moving the cannula holder from its first terminal position to its second terminal position and a connecting means for receiving the active substance solution from the conveying unit, the connecting means configured to pass through the housing. The connection channel means fluidically communicates the connecting means with the cannula, when the cannula holder is positioned in its second terminal position, thereby permitting the active substance solution to be introduced into the patient and does not fluidically communicate the connection element with the cannula when the cannula is positioned in its first terminal position.

In a preferred embodiment, the advancer means comprises a retaining and releasing mechanism, which includes a spring loaded catch with a lock positioned to retain the cannula holder in the first terminal position and a spring positioned to bias the cannula holder toward the base.

In an additional embodiment, the connection channel means comprises two conduits, an end of each conduit fluidically connected to each other when the cannula holder is positioned at its second terminal position and not fluidically connected when the cannula holder is positioned at its first terminal position, the other end of the first conduit being fluidically connected to the connecting means.

The subject invention will now be described in terms of its preferred embodiments. These embodiments are set forth to aid in understanding the invention, but are not to be construed as limiting.

Figure 1:
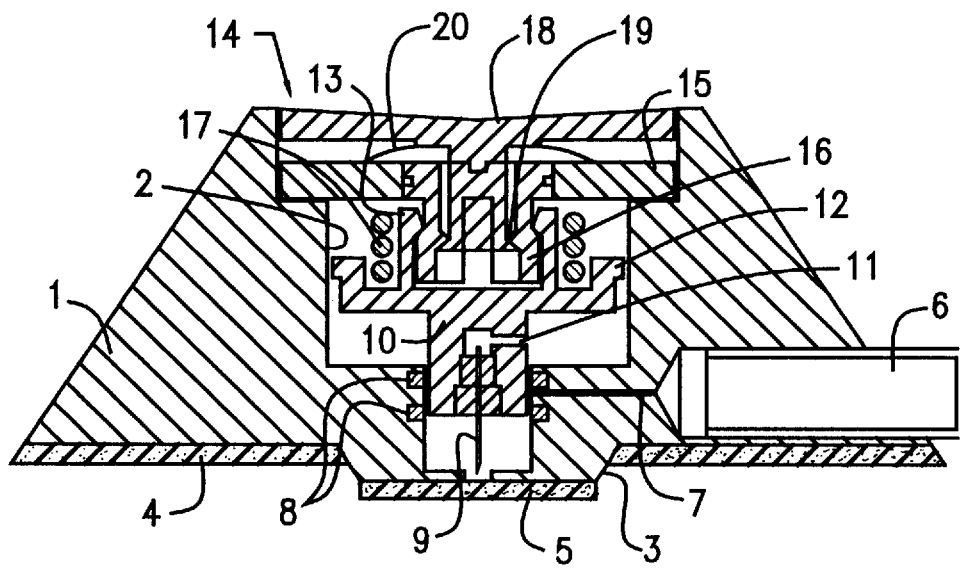
FIG. 1 shows a cross sectional view of an injection device in accordance with the invention.

The device shown in FIG. 1 has an approximately frustoconical housing 1 with a concentric bore or cavity 2 which consists of four regions with diameters increasing in each case from the base (adjacent to and contacting skin) to the top. The base of the housing has a concentric projection 3. The part of the base which surrounds the projection 3 is provided with an adhesive layer 4 for fastening the device to a site on a patient's body, such as the skin. In particular, the material and thickness of the adhesive layer 4 is selected in accordance with conventional practice with a view to wearing convenience and secure retention of the device. In the embodiment of FIG. 1, a so-called adhesive foam was selected for layer 4. The surface of the projection 3 is likewise provided with an adhesive layer 5 which serves in particular for reliable immobilization of the skin. For this purpose, the adhesive layer 5 consists of a thinner, relatively strong bonding adhesive material. However, adhesive layers 4 and 5 may consist of the same material.

A Luer attachment 6 is located at a site on housing 1 and serves to connect the device to a delivery pump (not shown) for an active substance solution and, via the latter, to a reservoir (not shown). Besides a Luer attachment, the invention contemplates all releasable securing mechanisms, such as, sealable bayonette attachment with, if necessary, O rings. A narrow channel 7 leads from the Luer attachment 6 to the central bore 2. Above and below the opening of the channel 7 into the bore, O rings 8 are inserted into corresponding annular grooves in the inner wall of the bore.

A thin steel capillary of about 200 $\mu$ diameter with a beveled insertion end serves as cannula 9. The cannula is fixedly secured in a cannula holder 10. The cannula holder 10 is an element which is arranged to be concentrically and axially displaceable in the bore 2 and which is shown in FIG. 1, in its upper terminal or first position away from the skin. In its lower or second terminal position, the lower face of the cannula holder lies on a stop formed by the junction between the narrowest region of the bore 2 and the next larger one thereof. In this lower position, the cannula 9 then is positioned and dimensioned to extend through the narrowest region, serving as passage for the needle, of the bore 2 and through the adhesive layer 5, for example, so as to penetrate into the tissue of the adjoining skin of a patient.

A channel 11 leads from the cylindrical side of the cannula holder 10 and widens in the interior thereof. The end of the cannula 9 opposite to the beveled tip thereof opens into the widened section of channel 11. In the lower or second terminal position of the cannula holder, the outer opening of channel 11 is opposite to and aligns with the inner opening of channel 7 in the housing 1, so that channel 11 and 7 are in fluid communication with each other.

The cannula holder 10 has a guide flange 12 with a diameter corresponding to the internal diameter of the third region of bore 2. On its upper surface, the cannula holder 10 has a hollow cylindrical wall 13 which is provided on its inside directly adjacent to its upper end with an encircling beading. The wall 13 with the beading cooperates with retaining and releasing mechanism 14 which will be described hereinafter.

A retaining and releasing mechanism 14 is inserted into the topmost region of bore 2 with the largest diameter and retains the cannula holder 10 in the resting state in its upper or first terminal position and, by releasing, permits its displacement into the lower or second terminal position. Between the cannula holder 10 and the retaining and releasing mechanism 14 there is a coil spring 17 which biases the cannula holder 10 downwards toward the base of housing 1.

The retaining and releasing mechanism 14 consists of two parts which can be displaced axially towards one another and of which the lower consists of an annular plate 15 and elastic wall segments 16 which project downwards toward the base of housing 1 on the central opening of the latter and essentially form a hollow cylindrical shape. The plate 15 is firmly connected to the housing 1, for example, screwed, welded and the like. It forms the upper abutment of the spring 17 and must therefore be designed to be relatively rigid with respect to the pressure applied by the plate.

The wall segments 16 have on their outer and upper surfaces a conical shoulder which forms the junction between an upper smaller and a lower larger axial distance. The beading of the wall 13 lies on this shoulder, which retains the cannula holder 10 in its upper terminal position. The wall segments 16 likewise have on their inside a shoulder in which a bracing flange 19, which will be described hereinafter, engages.

The upper part of the retaining and releasing mechanism 14 consists of an approximately mushroom-shaped releasing trigger or button 18 on the lower end of which the said bracing flange 19 is located. The releasing trigger is retained in the upper position shown by a disc spring 20. The bracing flange 19 prevents the inward movement of the elastic wall segments 16 and thus the releasing of the downward movement of the cannula holder 10 toward the base of housing 1.

The retaining and releasing mechanism 14 accordingly represents, in the present embodiment, a spring-loaded catch with lock as will be described below. Removal of the lock automatically releases a spring-loaded catch as a result of the pressure of the spring 17.

If the device is attached (that is to say adhered) to a suitable site on a patient's body, and is connected to a conveying unit (not shown) for retention of an active substance solution, and if the injection is to be triggered, the patient pushes the trigger 18 downwards toward the base against the pressure of the spring 20. This pushes the bracing flange 19 out of its seating in the interior of the elastic wall segments 16. The wall segments collapse inwardly from the pressure exerted on the shoulder by the coil spring 17 via the beading. The cannula holder 10 together with the cannula 9 is pushed downwards toward the base with high acceleration by the spring 17. The cannula 9 is projected through the adhesive layer 5 into the patient's tissue. The high acceleration means that the penetration of the needle takes place so quickly that the patient feels no pain.

Figure 2:
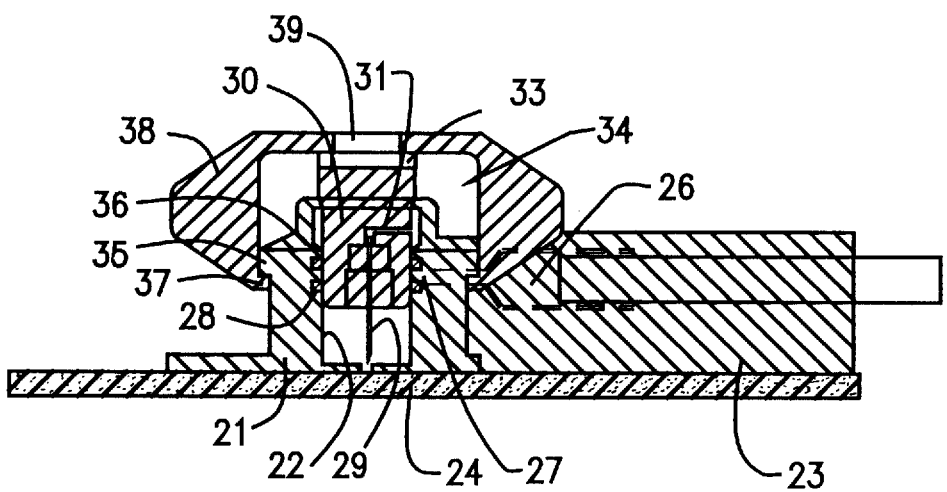
FIG. 2 shows a cross sectional view of an additional embodiment of an injection device in accordance with the invention comprising a viewing window from which a patient can determine if the cannula has been inserted.

The additional embodiment shown in FIG. 2 has a number of functional elements identical to those shown in FIG. 1. Some of the elements merely have a different shape, while other elements are assigned different or additional functions.

A housing 21 has a bore 22 which, in the present case, has only one gradation of its diameter, namely the constriction at its lower end to form an orifice for an injection cannula 29. The housing is likewise provided on its underside with an adhesive layer 24 which in this case is designed to be continuous with the entire base. A Luer attachment 26 is located in an extension 23 attached on the side of the housing and is connected via a channel 27 to the bore 22. Two O rings 28 lie in corresponding annular grooves above and below the opening of the channel 27 into the bore 22.

The cannula 29 is also in this case seated in a cannula holder 30 which is designed to be essentially cylindrical and has a channel 31 for connecting the rear of the cannula to the bore 22. The outer surface of bore 22 has a conical shoulder formed by an upward widening of its cross section. The cannula holder 30 is firmly connected via an annular, glass-clear or transparent viewing element 33 to a cap 38 which encloses the entire mechanism and which can be moved downwards from the upper or first position shown in FIG. 2 and serves as a releasing or trigger head. The cap 38 has a viewing window 39 in its center.

Elastic wall segments 36 are located on the housing surface and arranged around the edge of the bore 22, and are provided on their upper edge with projections which are directed towards the axis and which grip under the conical shoulder of the cannula holder 30. The wall segments 36 are elastic and form together with the conical shoulder of the cannula holder, a retaining and releasing mechanism 34. Finger pressure on the cap 38 bends them outwards until, when the pressure is sufficient, they release the cannula holder 30. Owing to the finger pressure necessary to overcome the retaining force, when the cannula holder 30 is released, the needle is forced into the patient's skin. The upper end of the cannula holder 30 adjacent viewing element 33 has a conical taper and is designed so that the elastic wall elements 36 exert a pressure directed downwards onto the cannula holder, which holds the needle in the lower or second insertion position after pushing in.

The outer surface of the cap 38 is shaped so that it can be gripped by the fingers and pulled back again to its initial position. On its lower edge, the cap 38 is provided with a projection 37 which is directed inwards and which, together with a corresponding shoulder 35 on the housing, prevents the cap being pulled out beyond the initial position. The result of this is that the cannula manually can be pulled back completely into the housing again after the infusion is complete.

In the lower terminal position of cap 38 and cannula holder 30, the projections on the wall segments 36 are at the level of the viewing element 33 and are in contact with it. The wall segments 36 are manufactured in a preselected color so that they are readily visible in this position through the viewing window 39 and thus indicate that the cannula 29 has been inserted. A visual check of this type is often advantageous because the patient does not feel the prick of the needle.

Figure 3A:
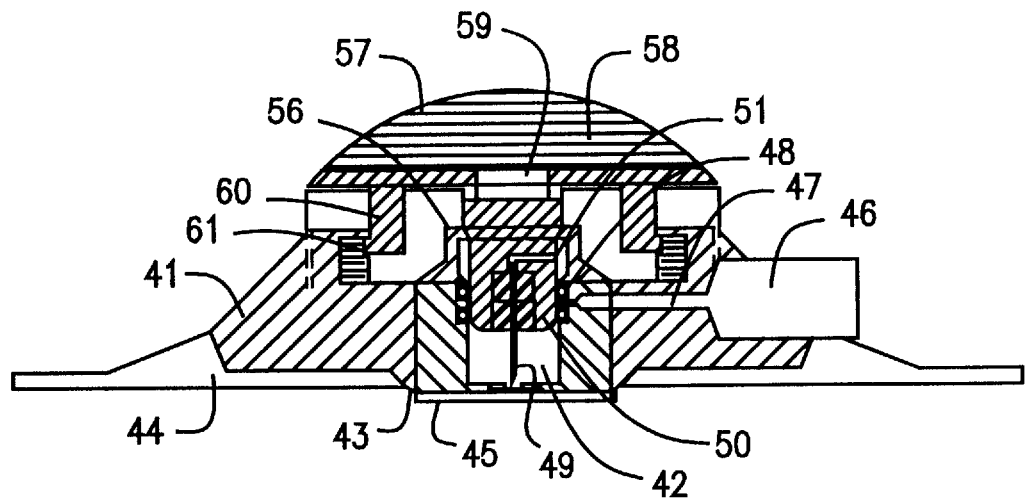
FIG. 3a shows a cross sectional view of an additional embodiment of an injection device in accordance with the invention having an alternative mechanism for insertion of the cannula into the patient.
Figure 3B:
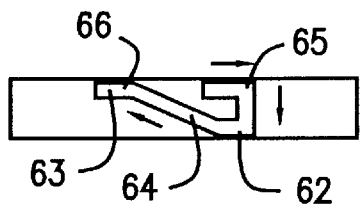

FIG. 3a shows a device in which the housing 41 has a design very similar to that in FIG. 1 with bore 42, projection 43, adhesive layers 44 and 45 and with Luer attachment 46, channel 47 and O rings 48 in the wall of the bore 42. The cannula holder 50 with cannula 49 and connection channel 51 and the wall segments 56 retaining it are the same as in the device shown in FIG. 2. The cap 57, which also has a viewing window 59 in this case, is provided with a crossbar 58 by which cap 57 can be rotated. The cap 57 additionally has a plurality of fingers 60 which project downwards from its underside toward the base and which in turn are provided with toes 61 which are directed radially outwards. These toes 61 slide in grooves provided in the wall of the upper region of the bore and of which one is shown in FIG. 3b. The groove has an arm 62 which runs vertically downwards and an arm 63 which is inclined like a ramp. The two arms are connected at the bottom by a short horizontal piece 64. A horizontal groove piece 65, 66 is attached at each of their upper ends. The horizontal groove piece 65 on the right in the drawing, which is located at the top of the vertical arm 62, defines the resting or first terminal position before use of the device. The other horizontal groove piece 66 at the top of the inclined arm 63 defines the position after use of the device. The cannula holder 50 and injection cannula 49 are pulled back into the resting or first position by rotating the crossbar 58 before the device is taken off the patient. This pulling back of the cannula prevents both possible injury to the patient due to tilting of the cannula on taking off, and injuries and thus infections of the medical assistants owing to a projecting cannula.

Figure 4:
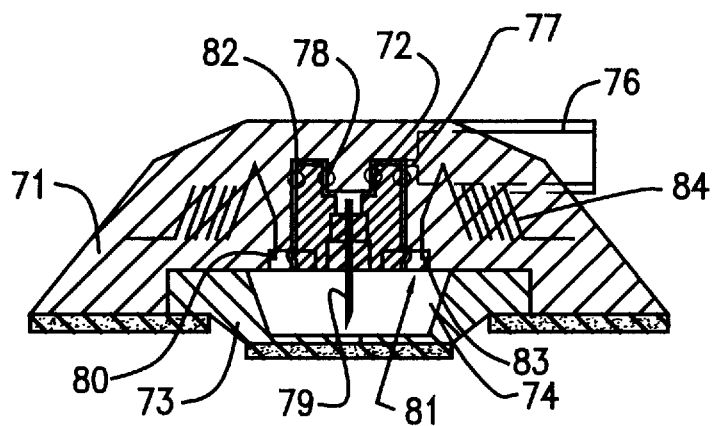
FIG. 4 shows a cross sectional view of an additional embodiment of an injection device in accordance with the invention having a flat housing 71 and no manual release of the cannula.

The device shown in FIG. 4 has no release of the cannula advance to be actuated manually by the patient. The housing 71 is very flat, only about 10 mm high, and is closed at the top and has a concentric chamber 72 open at the base (adjacent skin contact). The housing 71 is in two parts and has a part 73 which is inserted in the base and simultaneously forms a projecting part, surrounding the orifice, of the base. A protective film 74 is located between the main part of the housing 71 and the inserted part 73 and encloses the chamber formed between the two parts. A Luer attachment 76 is located in the upper part of the housing 71 and is connected by a channel 77 to the chamber 72.

An O ring 78 is inserted into a corresponding encircling groove on a concentric projection projecting from above into the chamber.

A cannula 79 is seated in a catnnula holder 80 which essentially matches the shape of the chamber 72. The cannula holder 80 has on its lower edge an encircling projection which engages in a corresponding annular groove in the housing and forms, together with the groove, a spring-loaded catch 81. The latter retains the cannula holder firmly in the position shown in the resting state or first terminal position.

Near the upper edge of its cylindrical outer surface, the cannula holder 80 has an encircling annular groove into Which an O ring 82 is inserted. In housing 71 adjacent the inner wall of the cannula holder 80 there are encircling grooves into Which O ring 78 is inserted. An annular enclosed space is produced by the two O rings 78 and 82 between the cannula holder 80 and the upper face of the chamber and is connected to the Luer attachment 76 only through the channel 77.

The cannula holder 80 furthermore has on its lower edge, toward the base of housing 71, two pins 83 which project radially outwards. The end pieces of two torsion springs 84 engage these. The latter have an initial tension such that they convey the cannula holder downwards toward the base of housing 71 as soon as it is released.

This embodiment of FIG. 4 functions in the following way:

When the device is fastened to a site on the patient's body, the connection to the conveying unit for tithe active substance solution (not shown) is set up via the Luer attachment. The delivery pump (not shown) generates a pressure in the upper region of the chamber 72. The force acting thereby on the cannula holder 80 is added to the force of the springs 84. As soon as the added force exceeds the retaining power of the spring-loaded catch 81, the cannula holder moves downwards toward the base of housing 71. The springs 84 now take over the propulsion of the cannula holder. After an initial short distance has been covered, the inner upper rim of the cannula holder has passed below the O ring 78 and thus opens the way for the active substance solution to flow to the upper end of the cannula 79. The active substance solution is able to reach the patient's skin through the cannula 79.

Figure 5A:
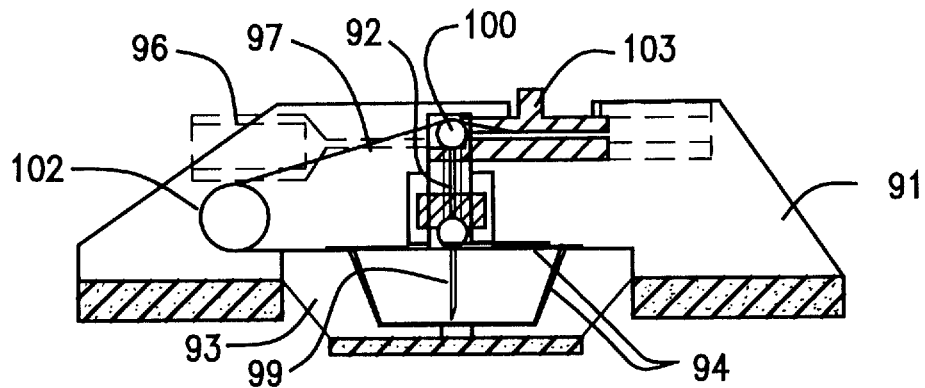
FIG. 5a shows a cross sectional view of an additional embodiment of an injection device in accordance with the invention having a flat housing 71 comprising a lower part 93 and upper part 91.
Figure 5B:
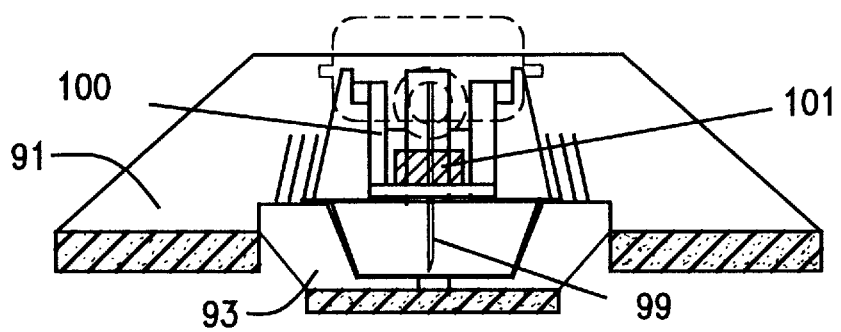

The device shown in FIG. 5 is depicted in two mutually perpendicular cross-sections in order to make the details clearer. The aim of this device was to reduce the height of the construction even further. The housing 91 is very flat, that is, it has a height of less than 10 mm. A chamber 92 (central cavity) which is centrally located in the housing 91 is open at the bottom (base) and closed at the top. The housing 91 is in two parts for assembly. The lower part 93 forms a central, concentric projection which projects beyond the face of the base of housing 91. Protective films 94 are located between the lower part 93 and the main part of the housing 91 and seal the cavity produced between the two housing parts. A Luer attachment 96 is again located in the upper housing part 91 and is connected by a channel 97 to the chamber 92.

A cannula 99 is inserted in a cannula holder 100 but otherwise moves freely in an elastic seal 101 located in the lower part of the chamber 92.

The cannula holder 100 essentially consists only of a U-shaped element on the upper ends of whose arms there are located attachment points for the transmission of force from torsion springs 102. The springs 102 have an initial tension such that they drive the cannula holder 100 with the cannula 99 downwards, toward the base, as soon as they are released.

The cannula holder 100 is retained in the upper resting position shown in FIGS. 5a by a slide 103. When the slide 103 is moved to the right, it releases the cannula holder 100, and the spring 102 is able to move the cannula holder 100 together With cannula 99 downwards, toward the base, and thus insert the cannula 99 into the patient's skin.

We claim:

1. A device for introducing into a patient a liquid active substance received from an external conveying unit, which comprises:
   a) a housing having a central cavity and a base;
   b) means for adhering the base to the skin of a patient;
   c) a cannula holder located within the cavity, the cannula holder being configured and dimensioned to move from a first terminal position to a second terminal position;
   d) a cannula secured to the cannula holder, the cannula being configured and dimensioned so that when the cannula holder is at the first terminal position, the cannula does not pass through the base, and when the cannula holder at the second terminal position, the cannula passes through the base, and when the base is adhered to the skin of a patient, into the skin of the patient;
   e) advancer means located within the cavity for moving the cannula holder from the first terminal position to the second terminal position;
   f) connecting means for receiving a liquid active substance from a conveying unit, the connecting means being configured and dimensioned to releasably secure the device to the conveying unit;
   g) a connection channel configured and dimensioned so that when the cannula holder is at the first terminal position, liquid active substance received by the connection means cannot flow from the connecting means through the connection channel into the cannula, and when the cannula holder is at the second terminal position, liquid active substance received by the connecting means can flow from the connecting means through the connection channel and into and through the cannula.

2. The device according to claim 1, wherein the advancer means comprises a retaining and releasing mechanism which includes a spring-loaded catch.

3. The device according to claim 2, wherein the spring-loaded catch comprises a lock positioned to retain the cannula holder in the first terminal position, and a spring positioned to bias the cannula holder toward the base.

4. The device according to claim 3, wherein the retaining and releasing mechanism further comprises a releasing button positioned to release the lock.

5. The device according to claim 4 further comprising a viewing window to determine the position of the cannula holder.

6. The device according to claim 2, wherein the retaining and releasing mechanism includes sidewalls projecting toward the base and having a plurality of toes projecting outwardly from the sidewalls, the housing having a groove for receiving the toes.

7. The device according to claim 1, wherein the connection channel comprises, two conduits, a first conduit and a second conduit, each conduit having a first end and a second end, the first ends being fluidically coupled when the cannula holder is positioned at the second terminal position and not fluidically coupled when the cannula holder is positioned at its first terminal position, the second end of the first conduit being fluidically coupled to the cannula, and the second end of the second conduit being fluidically coupled to the connecting means.

8. The device according to claim 1, wherein the connection channel fluidically communicates with the cavity when the cannula holder is in the.

9. The device according to claim 8, wherein the advancer means is configured and dimensioned to advance the cannula holder from the first terminal position to the second terminal position based on the pressure of the active substance solution within the cavity.

10. The device according to claim 1 further comprising a film secured to the base to protect the cannula when the cannula holder is positioned at the first terminal position.

* * * * *

UNITED STATES PATENT AND TRADEMARK OFFICE
CERTIFICATE OF CORRECTION

PATENT NO. : 5,848,990
DATED : December 15, 1998
INVENTOR(S) : Giorgio Cirelli, Benno Rothenhäusler, Hans Steffen It is certified that error appears in the above-identified patent and that said Letters Patent is hereby corrected as shown below:

In claim 8, column 8, line 47, after "the cannula holder is in the" please insert -- second terminal position --.

Signed and Sealed this

Thirtieth Day of March, 1999

Attest:

Q. TODD DICKINSON

Attesting Officer

Acting Commissioner of Patents and Trademarks